(12) United States Patent
Beecher et al.

(10) Patent No.: US 6,322,363 B1
(45) Date of Patent: Nov. 27, 2001

(54) DENTAL PLIERS

(76) Inventors: Candace L. Beecher, 2197 Eiffel Cir., Upland, CA (US) 91784; Jawn P. Swan, 10723 Stradella Ct., Belair Estates, CA (US) 90077

( * ) Notice: Subject to any disclaimer, the term of this patent is extended or adjusted under 35 U.S.C. 154(b) by 0 days.

(21) Appl. No.: 09/560,582

(22) Filed: Apr. 28, 2000

Related U.S. Application Data

(60) Provisional application No. 60/131,625, filed on Apr. 28, 1999.

(51) Int. Cl.[7] ........................................ A61C 3/14
(52) U.S. Cl. ........................ 433/159; 433/162; 606/210
(58) Field of Search ........................ 433/162, 4, 157, 433/159; 606/210, 211; 294/99.2

(56) References Cited

U.S. PATENT DOCUMENTS

| | | | |
|---|---|---|---|
| 2,943,521 | * 7/1960 | Betton | 294/99.2 |
| 4,001,940 | * 1/1977 | Cusato | 433/162 |
| 5,385,471 | * 1/1995 | Chuen | 433/153 |
| 5,893,853 | * 4/1999 | Arnold | 606/210 |

* cited by examiner

*Primary Examiner*—John J. Wilson
(74) *Attorney, Agent, or Firm*—Christie, Parker & Hale, LLP

(57) ABSTRACT

A tweezer-like dental pliers having a pair of elongated, flat and generally parallel handles with connected first ends, spaced-apart central portions, and second ends with normally closed gripping tips. The second ends are bent at an acute angle, preferably about 70 degrees, with respect to the handles, and a projecting fulcrum contacts the handles adjacent the bend so the gripping tips can be separated by squeezing the handle central portions together. A screw engaged between the handle central portions adjustably limits separation of the central portions to control gripping pressure of the normally closed tips.

5 Claims, 2 Drawing Sheets

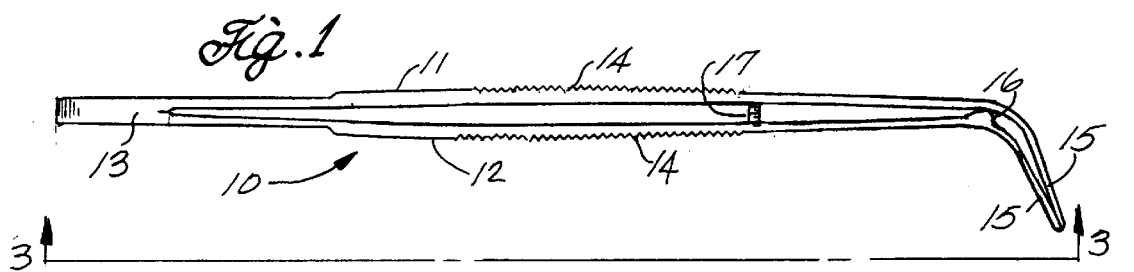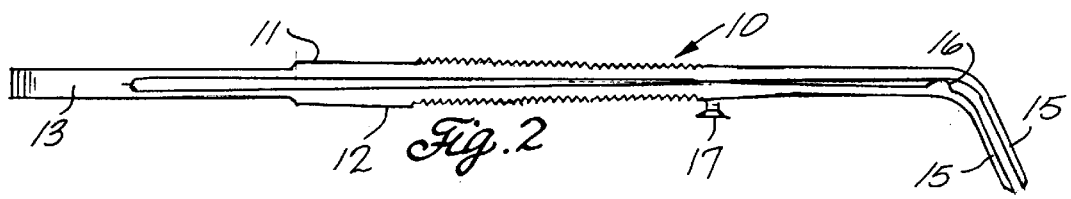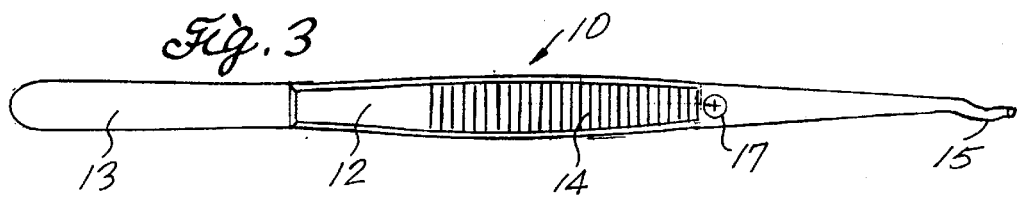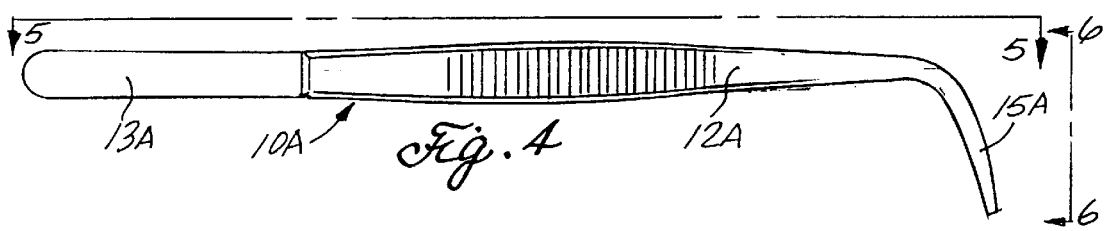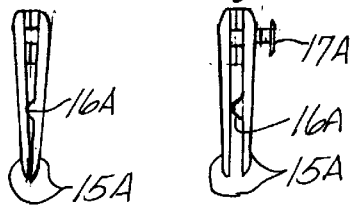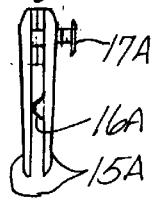

DENTAL PLIERS

CROSS-REFERENCE TO RELATED APPLICATION

This application claims the benefit of of Provisional Application No. 60/131,625, filed Apr. 28, 1999.

BACKGROUND OF THE INVENTION

The devices described herein came about because of a need to enable and simplify the placement of a product marketed under the trademark PerioChip® on anterior teeth, and especially on the mesial and distal surfaces of posterior teeth. The PerioChip product (made by Perio Products Ltd., in Israel, and marketed in the United States by Astra Pharmaceuticals, LP) is a small and thin chip of medication (chlorhexidine gluconate) which can be inserted in periodontal pockets between the teeth and surrounding gingival tissue. The chip is approximately square with a slightly rounded leading edge for ease of insertion, and typically measures about 4 mm×5 mm×350 μm. The chip is relatively easy to insert in accessible periodontal pockets of the anterior teeth, but difficult to grip securely for precise and gentle placement in the pockets of posterior teeth.

Described below are several different embodiments of a chip gripping and placement tool which is essentially a modification of a standard dental cotton pliers (the term "pliers" is conventional in dentistry, though the tool is nonpivoted, and can also be called a tweezers or forceps). Though referred to herein as a "dental pliers," the invention is not limited to dental applications, and is useful to grip and place a variety of small objects.

For placement on all anterior surfaces and the lingual and buccal of posterior teeth, the non-serrated or serrated tips, Teflon-coated or non Teflon-coated tips of the cotton pliers have been angled inward to an angle of 70 degrees, while the tips themselves have been made thinner while maintaining their width. Handles of the pliers have been altered by adding a small fulcrum point to one handle adjacent the bend of the tips, and a small movement-limiting screw approximately one-third of the way up the handles. These four modifications allow a closed or clamped position of the tips in the resting or relaxed mode, and an open mode with the tips spaced apart in the range of 1 to 3 millimeters (easily expanded to 6 or 7 millimeters should wider spacing be desired) with the tool handles squeezed together. Gentle pressure is applied to the handles of the placement pliers thus opening the tips to allow the practitioner to pick up the chip, release the handles thereby locking the chip in place without fear of dropping it before it reaches the mouth, placing the chip in a desired location of a periodontal pocket, and again pressing the handles together to release the chip and remove the placement pliers.

For easier placement of the chlorhexidine chip on the mesial and distal surfaces of the posterior teeth, and labial and lingual surfaces of the anterior teeth, the cotton pliers are altered by turning the serrated or non-serrated, Teflon-coated or Teflon-free tips about 90 degrees from their original position, then downward to about a 70-degree angle, while the tips themselves have been made thinner while maintaining their width. The handles have been altered by adding a small fulcrum point to an inner surface of one of the tips adjacent the bend of the tips, and a small screw approximately one-third of the way up the handles. These four modifications allow a closed position at the tips in the resting mode, and an open position of 1–3 mm in the open mode. The application of the chip would proceed as described for the pliers designed for the anterior surfaces, and the posterior buccal or lingual surfaces.

Note that from the alterations described, while the handles of the anterior, buccal and lingual placement pliers would maintain their original position of vertical placement, one side by side of the other, the handles of the posterior mesial and distal placement pliers would be in a horizontal position, one on top of the other.

SUMMARY OF THE INVENTION

The pliers of this invention comprises a pair of elongated and generally parallel flat handles having first ends which are secured together, and second ends terminating in opposed gripping tips. The handles are resiliently loaded such that the tips are normally closed together, and the handles between the first and second ends have central portions which are urged apart. The handles have bent portions so the second ends, while remaining adjacent and generally parallel, extend at an acute angle from gripping surfaces of the handle central portions which can be squeezed toward each other. A fulcrum-like projection is positioned adjacent the bent portion of one of the handles to extend into contact with the other handle so the tips are separated when the handle gripping surfaces are squeezed toward each other. A screw or similar means is engaged between the handles for adjustably limiting separation of the cental portions of the handles, and thereby to control gripping force of the normally closed tips.

DESCRIPTION OF THE DRAWINGS

FIG. 1 is a side elevation of a first embodiment of a pliers according to the invention, and in a relaxed position with engaged gripping tips;

FIG. 2 is a side elevation similar to FIG. 1, but showing arms of the pliers squeezed toward each another to open the gripping tips;

FIG. 3 is a view on line 3—3 of FIG. 1;

FIG. 4 is a side elevation of a second embodiment of the pliers;

FIG. 5 is a view on line 5—5 of FIG. 4;

FIG. 6 is an end view on line 6—6 of FIG. 4 with the tool arms relaxed to close the gripping tips;

FIG. 7 is a view similar to FIG. 6, but with the tool arms squeezed together to open the gripping tips;

DESCRIPTION OF THE PREFERRED EMBODIMENTS

Figure 8:
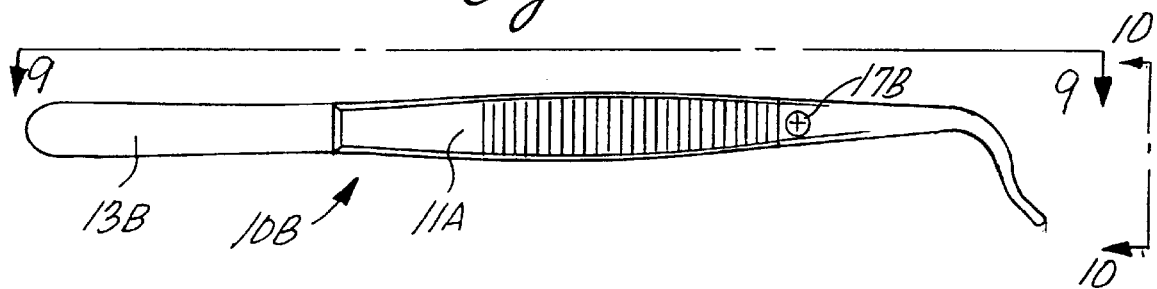
FIG. 8 is a side elevation of a third embodiment of the pliers with doubly curved tips.

A first embodiment of a dental pliers 10 according to the invention is shown in FIGS. 1–3, and is in many respects similar to a conventional tweezers in having a pair of opposed and elongated blade-like arms or metal handles 11 and 12 extending from and joined together at first ends by a base portion 13. Generally flat outer surfaces of the handles are preferably formed with conventional serrations 14 for ease of gripping during use. Beaks or tips 15 at second ends of the handles are angled about 70-degrees downwardly (from a central longitudinal plane of the pliers extending between and generally parallel to the flat surfaces of the handles)as seen in FIGS. 1 and 2. A bump-like projection on an inner surface of an inner end of one of the tips and slightly toward base portion 13 forms a fulcrum 16. A screw 17 has a shank extending through a clearance hole in one of the handles, and a conical head seated in a mating conical recess in that handle. The other end of the screw is threaded into a mating threaded opening in the other handle.

Handles 11 and 12 are normally spring biased away from each other as shown in FIG. 1 to position tips 15 against each other to grip a chip (not shown) as described above. Screw 17 is adjusted to limit the displacement of the handles away from each other, and thereby to regulate the gripping pressure exerted by the closed tips. To open the tips to grip or release a chip or similar object, the handles are manually squeezed together as shown in FIG. 2. In this position, fulcrum 16 causes the tips to separate as illustrated. Pliers 10 is well suited for chip insertion.

A second embodiment of a dental pliers 10A is shown in FIGS. 4–7, and is similar to pliers 10, with the exception that tips 15A are differently angled to remain in the general planes of the flat sides of handles 11A and 12A. Fulcrum 16A is also repositioned to be placed between the bend of tips 15A and the distal ends of the tips.

Figure 9:
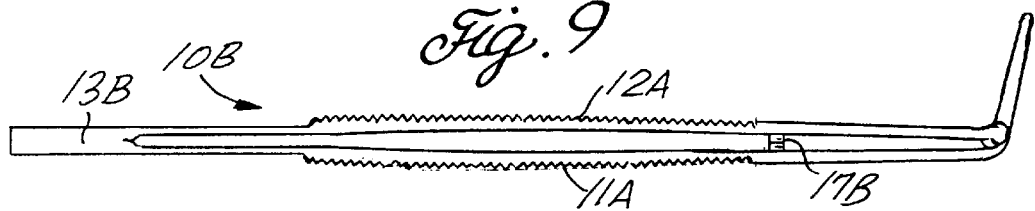
FIG. 9 is a view on line 9—9 of FIG. 8.
Figure 10:
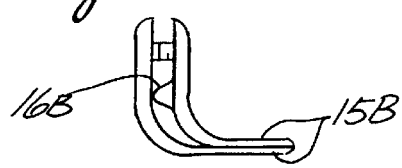
FIG. 10 is an end view on line 10—10 of FIG. 8 with the tool arms relaxed to close the gripping tips.
Figure 11:
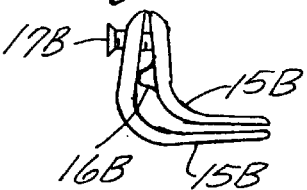
FIG. 11 is a view similar to FIG. 10, but with the tool arms squeezed together to open the gripping tips.

A third embodiment of a dental pliers 10B is shown in FIGS. 8-11, and is similar to pliers 10A, but with doubly-curved tips 15B, fulcrum 16B being positioned between the first and second bends of the pliers tips.

What is claimed is:

1. A tweezer-like dental pliers, comprising:

a pair of elongated handles having first and second ends, the handles having central portions in separated face-to-face positions, the first ends being secured together to resiliently urge flat inner-surface tips of the second ends together in a normally closed position to grip an object to be held, the handles being bent at an acute angle adjacent the second ends while remaining generally parallel;

an inner surface of one of the handles having a rigid projection secured thereto and facing an inner surface of the opposed handle, the projection forming a fulcrum whereby the normally closed tips are separated when the handles are squeezed together; and means connected between the handles for adjustably limiting separation of the handles to adjust gripping force of the tips.

2. The pliers defined in claim 1 wherein the projection is positioned slightly toward the first ends and adjacent the handle bends.

3. The pliers defined in claim 1 wherein said means is a screw with a head and a shank, the shank being threaded into one of the handles, and passing through a clearance hole in the other handle, the screw head being positioned against the other handle.

4. The pliers defined in claim 1 in which the angle at which the handles are bent adjacent the second ends is about 70 degrees.

5. A tweezer-like dental pliers, comprising:

a pair of elongated handles having first and second ends, the handles having central portions in separated face-to-face positions, the first ends being secured together to resiliently urge the second ends together to grip an object to be held, the handles being bent at an acute angle adjacent the second ends while remaining generally parallel;

one of the handles having a projection facing the opposed handle, the projection being positioned between the handle bends and the tips, the projection forming a fulcrum whereby the normally closed tips are separated when the handles are squeezed together; and means connected between the handles for adjustably limiting separation of the handles to adjust gripping force of the tips.

* * * * *